US010492374B2

(12) United States Patent
Regan et al.

(10) Patent No.: US 10,492,374 B2
(45) Date of Patent: Dec. 3, 2019

(54) CAPTURE OF GROUND TRUTHED LABELS OF PLANT TRAITS METHOD AND SYSTEM

(71) Applicant: X Development LLC, Mountain View, CA (US)

(72) Inventors: William R. Regan, San Carlos, CA (US); Matthew A. Bitterman, Mountain View, CA (US); Benoit G. Schillings, Los Altos Hills, CA (US); David R. Brown, San Francisco, CA (US); Elliott Grant, Woodside, CA (US)

(73) Assignee: X DEVELOPMENT LLC, Mountain View, CA (US)

( * ) Notice: Subject to any disclaimer, the term of this patent is extended or adjusted under 35 U.S.C. 154(b) by 74 days.

(21) Appl. No.: 15/857,512

(22) Filed: Dec. 28, 2017

(65) Prior Publication Data
US 2019/0200535 A1 Jul. 4, 2019

(51) Int. Cl.
*A01G 7/00* (2006.01)
*G06K 9/00* (2006.01)
(Continued)

(52) U.S. Cl.
CPC ............. *A01G 7/00* (2013.01); *B64C 39/024* (2013.01); *G06K 9/00657* (2013.01); *G06N 3/08* (2013.01);
(Continued)

(58) Field of Classification Search
CPC ................. G06K 9/00657; A01G 7/00; G01N 2021/8466
See application file for complete search history.

(56) References Cited

U.S. PATENT DOCUMENTS 5,764,819 A * 6/1998 Orr ..................... G06K 9/0063
382/110
6,236,739 B1 * 5/2001 Conrad .................... G06T 7/62
382/110
(Continued)

OTHER PUBLICATIONS

Balboa et al., "Spatial-Temporal Evaluation of Plant Phenotypic Traits via Imagery Collected by Unmanned Aerial Systems (UAS)," The International Society of Precision Agriculture Presents the 13th International Conference on Precision Agriculture, Jul. 31-Aug. 4, 2016, 4 pages.
(Continued)

*Primary Examiner* — Nay A Maung
*Assistant Examiner* — Jose Torres
(74) *Attorney, Agent, or Firm* — Christensen O'Connor Johnson Kindness PLLC

(57) ABSTRACT

In embodiments, acquiring sensor data associated with a plant growing in a field, and analyzing the sensor data to extract, while in the field, one or more phenotypic traits associated with the plant from the sensor data. Indexing, while in the field, the one or more phenotypic traits to one or both of an identifier of the plant or a virtual representation of a part of the plant, and determining one or more plant insights based on the one or more phenotypic traits, wherein the one or more plant insights includes information about one or more of a health, a yield, a planting, a growth, a harvest, a management, a performance, and a state of the plant. One or more of the health, yield, planting, growth, harvest, management, performance, and the state of the plant are included in a plant insights report that is generated.

14 Claims, 6 Drawing Sheets

(51) Int. Cl.
*B64C 39/02* (2006.01)
*G06N 3/08* (2006.01)
*G06N 3/04* (2006.01)

(52) U.S. Cl.
CPC .......... *B64C 2201/127* (2013.01); *G06N 3/04* (2013.01); *G06N 3/0445* (2013.01); *G06N 3/0454* (2013.01)

(56) References Cited

U.S. PATENT DOCUMENTS

| | | | |
|---|---|---|---|
| 7,617,057 B2* | 11/2009 | May | A01G 7/00 702/62 |
| 7,715,013 B2* | 5/2010 | Glaser | G01N 21/314 356/448 |
| 7,916,898 B2 | 3/2011 | Anderson | |
| 8,902,413 B2 | 12/2014 | Ulman et al. | |
| 9,152,938 B2 | 10/2015 | Lang et al. | |
| 9,256,907 B2 | 2/2016 | Macy | |
| 9,619,734 B2 | 4/2017 | Marchsio et al. | |
| 9,792,557 B2 | 10/2017 | Mathur et al. | |
| 2007/0044445 A1* | 3/2007 | Spicer | A01G 7/00 56/10.1 |
| 2010/0324830 A1 | 12/2010 | Solie et al. | |
| 2011/0047636 A1* | 2/2011 | Stachon | A01G 7/00 800/260 |
| 2011/0125477 A1 | 5/2011 | Lightner et al. | |
| 2013/0028487 A1* | 1/2013 | Stager | B07C 5/342 382/110 |
| 2013/0067808 A1* | 3/2013 | Stachon | A01G 7/00 47/58.1 R |
| 2014/0294247 A1 | 10/2014 | Sirault et al. | |
| 2016/0247082 A1 | 8/2016 | Stehling et al. | |
| 2017/0032509 A1 | 2/2017 | Mannar et al. | |
| 2017/0090068 A1 | 3/2017 | Xiang et al. | |
| 2017/0161560 A1 | 6/2017 | Itzhaky et al. | |
| 2017/0213083 A1 | 7/2017 | Shriver et al. | |
| 2017/0223947 A1* | 8/2017 | Gall | G01N 21/4738 |

OTHER PUBLICATIONS

International Search Report and Written Opinion from the International Searching Authority dated Feb. 25, 2019 for International Application No. PCT/US18/65564, filed Dec. 13, 2018, 6 pages.

* cited by examiner

CAPTURE OF GROUND TRUTHED LABELS OF PLANT TRAITS METHOD AND SYSTEM

TECHNICAL FIELD

This disclosure relates generally to feature detection, and in particular but not exclusively, relates to use of computerized models for feature detection.

BACKGROUND INFORMATION

Sensor based systems configured to collect data about crops and plants growing outdoors, in fields, and/or other growing environments (referred to as raw data) may be capable of collecting large quantities of data. Raw data, in of itself, however, is not particularly useful. Determined insights about the crops and plants based on the raw data, on the other hand, may be of value.

Given the large quantity of raw data, it would be beneficial to automate determination of useful insights from the raw data. Automation schemes are useful to the extent that they produce accurate and reliable insights. In some embodiments, the accuracy and/or reliability of an automation scheme may depend upon large quantities of raw data that has been labeled, annotated, or otherwise identified with corresponding insight(s) that are known to be of high confidence or correct (also referred to as ground truth data or ground truthed labels). Acquiring such large quantities of ground truth data may be difficult. The available ground truth data may also suffer from inconsistency, non-uniformity, and/or other variability due to variability in the collection devices (e.g., the sensors experiencing calibration drift), changes in environmental conditions, and/or subjectivity among humans who may contribute to generation of the ground truth data. Improving the acquisition and/or quality of the ground truth data may improve the quality of one or more subsequent data generated about the crops and plants and/or uses of raw data.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

DETAILED DESCRIPTION

Embodiments of a system, apparatus, and method related to ground truthed labels of plant phenotypic traits are described herein. In embodiments, a method includes acquiring sensor data associated with a plant growing in a field, wherein the sensor data is acquired from one or more of an optical sensor, an acoustic sensor, a chemical sensor, a geo-location sensor, an environmental sensor, and a weather sensor; analyzing the sensor data to extract, while in the field, one or more phenotypic traits associated with the plant from the sensor data; indexing, while in the field, the one or more phenotypic traits to one or both of an identifier of the plant or a virtual representation of a part of the plant; determining one or more plant insights based on the one or more phenotypic traits, wherein the one or more plant insights includes information about one or more of a health, a yield, a planting, a growth, a harvest, a management, a performance, and a state of the plant; and generating a plant insights report that includes one or more of the health, the yield, the planting, the growth, the harvest, the management, the performance, and the state of the plant.

In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Figure 1A:
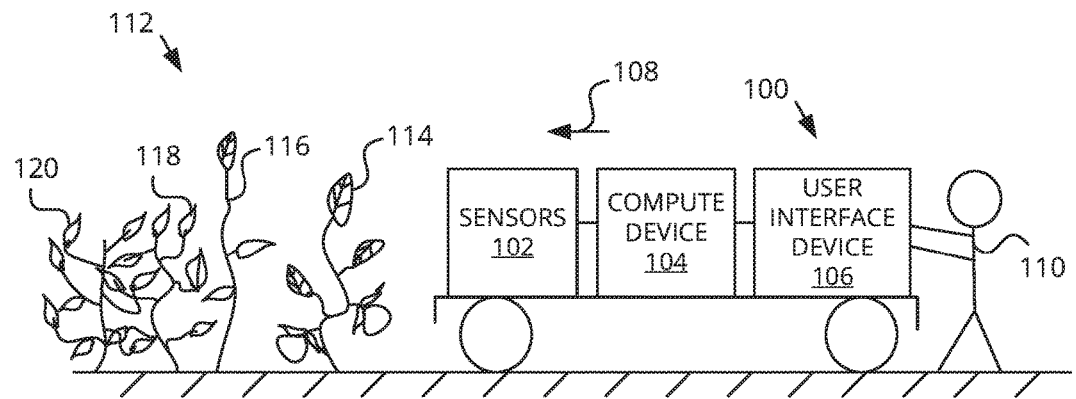
FIG. 1A depicts a block diagram illustrating an example mobile system incorporated with the ground truth labeling technology of the present disclosure, according to some embodiments.

FIG. 1A depicts a block diagram illustrating an example mobile system 100 incorporated with the ground truth labeling technology of the present disclosure, according to some embodiments. Mobile system 100 may be configured to be deployed in a plant or crop field environment to capture raw plant data and associated metadata along with contemporaneous generation of ground truthed labels of plant traits associated with the captured raw data. System 100 may traverse each row of plants (crops, crop plants, fruit bearing plants, vegetable bearing plants, or seed bearing plants) planted in a field in order to capture raw plant data and associated metadata about each plant included in a row, as will be described in detail herein. System 100 may also be referred to as a mobile platform, vehicle, cart, or the like.

In some embodiments, system 100 may include, but is not limited to, a compute device 104 in communication with each of the sensors 102 and a user interface device 106. Sensors 102 may comprise a plurality of sensors, detectors, cameras, and/or other devices capable of capturing one or more raw plant data and associated metadata (collectively referred to as raw data, raw sensor data, or sensor data). Sensors 102 may comprise, but are not limited to, passive sensors, active sensors, optical sensors for imaging or spectroscopy (e.g., red green blue (RGB) camera, multi-spectral imaging, hyper-spectral imaging, light detection and ranging (LIDAR), radar, thermal, infrared (IR), near IR, microwave, millimeter (mm)-wave, x-ray, etc.), acoustic sensors (e.g., ultrasound or lower frequency, etc.), chemical sensors (e.g., to capture plant, air, soil properties, etc.), geo-location sensors/devices/systems (e.g., global positioning system (GPS), GPS-real time kinematic (RTK), RTK-global navigation satellite system (GNSS), etc.), environmental and/or weather sensing devices/systems (e.g., to capture light, temperature, humidity, ground elevation, etc.), and/or the like.

Compute device 104 may comprise one or more devices capable of performing onboard processing and storage functions. Compute device 104 may include, without limitation, one or more processors and storage devices. At least a portion of the compute device 104 may comprises, for example, a laptop, tablet, mobile device, desktop computer, low cost computer (e.g., Raspberry Pi), computing device, graphical processing units (GPUs), tensor processing units (TPUs), machine learning (ML)-optimized chips, image processing optimized chips, and/or the like. In some embodiments, compute device 104 may be configured to process data captured by the sensors 102, store data, facilitate data to and from the user interface device 106, and/or the like.

In some embodiments, compute device 104 may additionally include one or more communication components, such as wireless communication components, so as to communicate with remote networks, servers, databases, geo-location satellite systems, and/or the like. For example, for processing intensive tasks that may exceed the processing capabilities or bandwidth of the compute device 104, such processing tasks may be performed by remote servers and the resulting data may be returned to the compute device 104 for subsequent uses. As another example, raw data captured by the sensors 102, ground truth labeled data generated at the system 100, phenotypes, plant traits, or insights extracted from the raw data, and/or the like may be backed up in databases located remotely from the system 100.

User interface device 106 may be configured to present one or more types of data to a human operator or user 110 and/or to facilitate receiving inputs from the user 110. Data to be displayed to the user 110 may be provided by the compute device 104 and data received from the user 110 may be provided to the compute device 104. User interface device 106 may include components to facilitate interfacing with the user 110. User interface device 106 may include, but is not limited to, a screen, touch screen, keyboard, mouse, joystick, microphone, graphical user interface (GUI), and/or the like. In some embodiments, user interface device 106 may be combined with the compute device 104. In alternative embodiments, user interface device 106 may include processing and/or storage functions, in which raw data from the sensors 102 and/or data from the compute device 104 may be processed to generate information appropriate for display on the user interface device 106.

System 100 may be configured to be mobile within a plant or crop field. System 100 may traverse a plant or crop field 112 that may be organized in a plurality of plant or crop rows. System 100 may traverse (e.g., in a direction 108) the field 112 a row at a time (or some other pattern), in which each plant or crop located therein may be sensed by the sensors 102. System 100 may be manually positioned (e.g., pushed) to respective plants by the user 110. Alternatively, or in addition to, system 100 may include transport mechanisms, such as an engine or motor, to facilitate automatic positioning of the system 100 to the plants. Plants 114, 116, 118, 120 included in the field 112 may be the same or different from each other.

System 100 may be configured to be positioned above, next to, and/or the like relative to the plant being sensed. In some embodiments, system 100 may sense plants 114-120 a plurality of times over a time period, thereby obtaining time series raw data associated with the same plants.

Figure 1B:
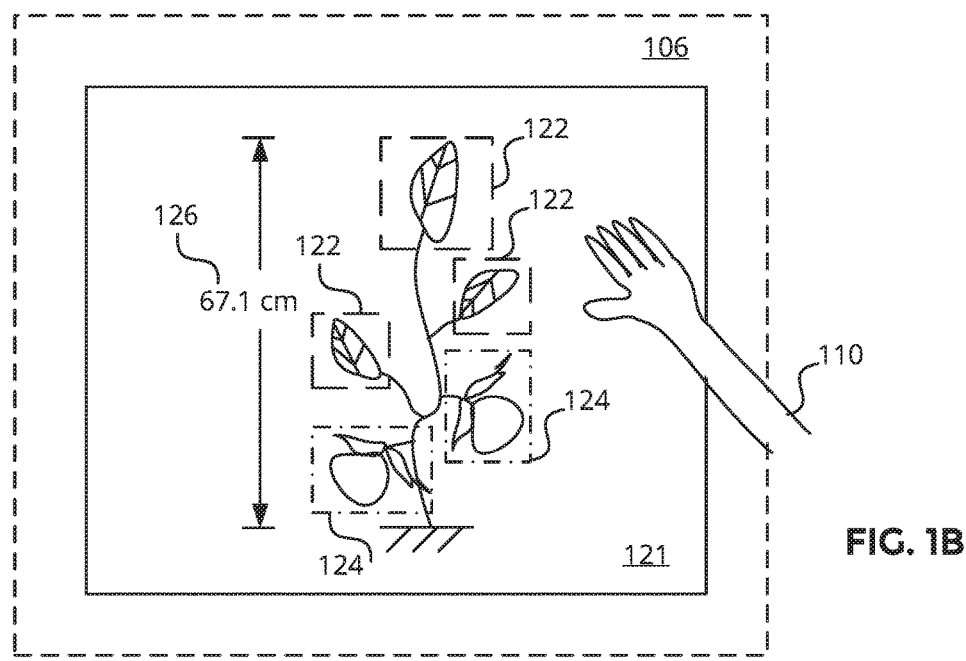
FIG. 1B depicts an example image displayed on an user interface device included in the system of FIG. 1 on which a user may enter ground truth labels, in accordance with some embodiments.

In some embodiments, system 100 may be configured for contemporaneous, real time, or near real time generation of ground truth labeled data associated with the raw data captured by the sensor 102. In particular, the ground truth labeled data may be manually provided by the user 110. FIG. 1B depicts an example image 121 displayed on the user interface device 106 on which the user 110 may enter ground truth labels, in accordance with some embodiments.

Image 121 may comprise an image of plant 114 based on at least a portion of the raw data captured by the sensors 102 of the plant 114. When the image of plant 114 is displayed to the user 110, user 110 may identify, annotate, label, or otherwise specify, via the user interface device 106, one or more ground truth labels for the plant 114. Ground truth labels may comprise identification, classification, and/or measurements of plant phenotypic traits that are of high confidence of being accurate or correct. In some embodiments, ground truth labels may be manually specified by the user 110 from looking at the plant 114 depicted in the image 121 (e.g., based on the sensed raw data) and/or direct observations or measurements taken on the actual plant 114.

For example, in FIG. 1B, user 110 may view the plant depicted in image 121, and add labels 122 to ground truth label the leaves (e.g., manually place a box around each leaf using a touchscreen, keyboard, mouse, etc.) and labels 124 to ground truth label the fruit. User 110 may also directly measure the height of the actual plant 114 with a yardstick, and enter the measured plant height as a ground truth label 126 on image 121. Accordingly, ground truth labels comprising plant phenotypes or traits associated with raw sensed data of a plant may be manually entered by a human operator, trained personnel, or the like.

Figure 2:
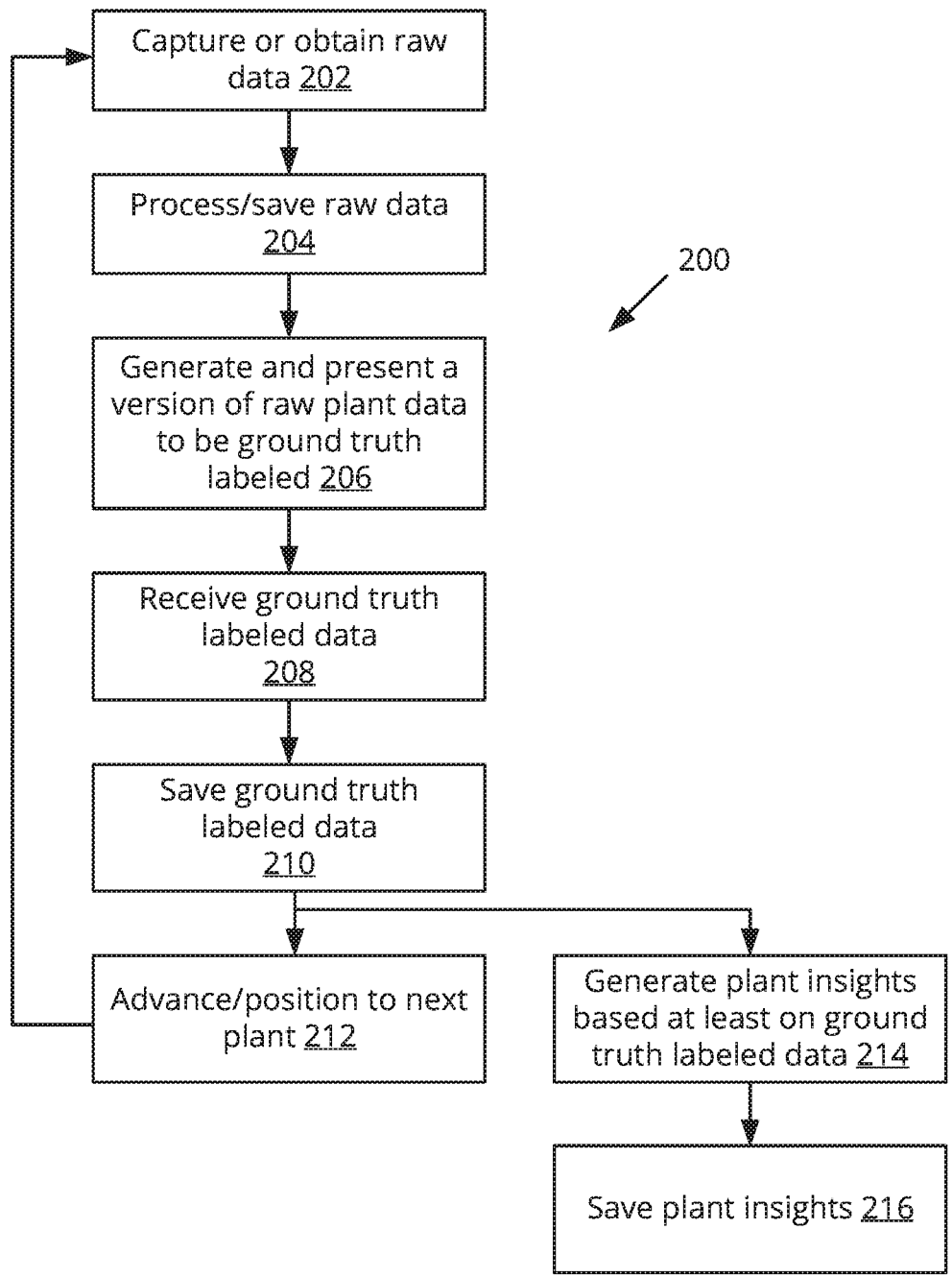
FIG. 2 depicts an example process for manual generation of real time (or near real time) ground truth labels, according to some embodiments.

FIG. 2 depicts an example process 200 for manual generation of real time (or near real time) ground truth labels, according to some embodiments. At block 202, raw data (also referred to as sensed data) associated with a particular plant (e.g., plant 114) may be captured, obtained, or acquired. As discussed above, raw data may comprise a variety of data sensed or collected about the plant and/or environment proximate to the plant. The raw data may be contemporaneous to each other. Raw data may comprise, but is not limited to: RBG images, normalized difference vegetation index (NDVI) images, multispectral images, hyper-spectral images, LIDAR images, radar images, thermal images, microwave images, mm-wave images, x-ray images, ultrasound or lower frequency acoustically sensed data of the plant and/or nearby surrounding area, chemical sensed data of the plant and/or nearby surrounding area (e.g., pH, moisture level, fertilizer composition, heavy metal content, or other soil properties), geo-location data, environmental or weather data (e.g., light, temperature, humidity, soil properties, solar incidence characteristics, etc.), three-dimensional (3D) point cloud plant data, and/or the like.

Raw data may be captured by the sensors 102 and/or obtained from remote source(s) facilitated by compute device 104.

Next at block 204, compute device 104 may be configured to process and/or save the raw data. For instance, at least a portion of the raw data may be filtered, calibrated, correlated with each other, tagged (e.g., a unique identifier assigned to each plant, associated with a time date stamp), indexed, otherwise processed, and/or the like. The raw and/or processed versions of the data may be stored locally at the system 100 and/or remotely.

Compute device 104 may generate a version of the raw or processed plant data that will be suitable for the user 110 to view and provide ground truth label(s), at block 206. An example of a suitable version may comprise one or more images of the plant associated with the raw data captured in block 202. In some embodiments, the suitable version may be displayed on the user interface device 106, such as the plant depicted in image 121 of FIG. 1B.

Next, at block 208, user interface device 106 may be configured to receive, from the user 110, ground truth labeled data associated with the plant depicted in the presented suitable version in block 206. In some embodiments, a plurality of images of the plant may be displayed and the user 110 may select a subset of images from the plurality of images to be ground truth labeled. Ground truth labels may specify, identify, or quantify one or more plant phenotypes or traits—the physical attributes or characteristics—of the plant of interest. Phenotype or phenotypic traits for plants or crops may include, without limitation, height, width, yield, chemical composition, health status (e.g., diseases), stress status (e.g., drought), quality (e.g., roundness of a strawberry), leaf count, leaf size, fruit size, flower size, fruit density, fruit count, stalk strength, and/or a variety of other attributes, some of which may be specific for the plant type or plant.

Ground truth labels may be entered in any of a variety of ways using, for example, a touchscreen, mouse, trackpad, joystick, physical keyboard, virtual keyboard, stylus, voice commands, and/or the like. Indications of the ground truth labels may also be of any of a variety of formats. For example, in image 121 shown in FIG. 1B, the user 110 may use his fingers to prescribe a box around each leaf of the plant (e.g., labels 122), prescribe a box around each fruit of the plant (e.g., labels 124), and enter a value for the measured height of the plant (e.g., label 126). As discussed above, manual ground truth labels may be based on direct observation of the raw data or processed raw data (e.g., viewing image(s) of the plant collected as part of raw data) and/or direct observation or measurements of the actual plant. Continuing the example of image 121, label 126 may be entered after measurement of the height of the actual plant by the user 110 using a yardstick or tape measure.

In some embodiments, blocks 206 and 208 may be performed contemporaneous with block 202 so as to generate ground truth labels in real time or near real time relative to raw data capture, while the plant of interest is in the same state, user 110 is proximate to the actual plant for direct observation and measurements, and/or the like. Blocks 202, 206, 208 may be performed during the same session of being in the field, without leaving the field, or the like. If images of the plant displayed on the user interface device 106 are faulty, for example, user 110 is in a position to initiate acquisition of new raw data, calibrate one or more of sensors 102, and/or the like rather than discovering at a (much) later point in time that raw data to be ground truth labeled are not suitable for performing ground truth labeling. Thus, inconsistencies, sensor calibration drift, or other factors may be minimized or addressed while in the field rather than afterwards away from the field or upon returning to the field after leaving.

Once the ground truth labels are manually specified, ground truth label data may be stored locally and/or remotely, at block 210. In some embodiments, processing of ground truth label data may occur to facilitate storage and later retrieval. For example, phenotypic traits of the ground truth labels may be indexed; associated with identifiers, time date stamps, user identifier, plant identifier, raw data, a virtual representation of respective parts of the plant, correlated or consolidated with each other; and/or the like. Raw data, processed raw data, ground truth labels, and potential processed ground truth labels may be associated with each other and stored in structured format to facilitate selective access.

Next at block 212, system 100 may be advanced to the next plant and process 200 may return to block 202 to obtain raw data associated with the new plant. System 100 may advance to the next plant incrementally, continuously, or periodically depending on the mobile capabilities of the system 100. Although raw data and ground truth labeling of a single plant is discussed above, it is understood that more than one plant may be simultaneously sensed or ground truth labeled.

Also proceeding from block 210 may be block 214, which may be performed on-site in the field environment, off-site, or after ground truth labels for a plurality of plants (e.g., for an entire row, entire field, etc.) have been generated. In some embodiments, compute device 104 and/or remote computing resources may be configured to generate one or more recommended intervention strategies, plant/crop management strategies or practices, or the like (collectively referred to as plant insights) based at least on the ground truth labeled data. Plant insights may be applicable to particular plants/crops, a plurality of particular plants/crops, particular field(s), and/or be time specific. In some embodiments, plant insights associated with a first plant may be based on one or more ground truth labeled data associated with the first plant, one or more ground truth labeled data associated with the first plant and one or more plants other than the first plant, one or more ground truth labeled data associated with the first plant and historical ground truth labeled data associated with the first plant, one or more ground truth labeled data associated with the first plant and historical ground truth labeled data associated one or more plants other than the first plant, and/or the like.

Plant insights may comprise predictions, recommendations, strategies, estimates, and/or information about one or more of a health, a yield, a planting, a growth, a harvest, a management, a performance, and a state of a plant of interest. For a given plant, its associated ground truth labels may be analyzed to determine whether one or more of the identified traits deviates from an ideal or expected normal state, and if a deviation is detected, access a knowledge base that specifies what action(s) may be taken to address the deviation. Leaf size, shape, color, or other traits may indicate, for instance, the presence of a particular disease. The knowledge base may specify what treatment may be taken to eliminate the particular disease from the plant, prevent the particular disease from spreading to other plants, prevent the particular disease from occurring in subsequently planted/grown plants, and/or the like. As another example, for a given plant, its associated ground truth labels may be analyzed to identify a particular state or status of the given plant. For a flowering plant (e.g., lilies), analyzing the size, shape, color, scent, or other traits of the flowers, leaves, stalk, or the plant overall may indicate how ready the flowers are for harvesting, and thus, an estimate may be made as to an ideal harvesting time of the flowers.

Examples of plant/crop insights may include, without limitation, (ideal) pruning schedule for the particular plant comprising a vine fruit, disease or insect identification and treatment strategy for the particular plant, fertilizer composition recommendation for a particular portion of the field that differs from fertilizers for a different portion of the field, increasing crop yield and/or quality by changing planting density and/or plant types in particular areas of the field based on micro-climate or micro-growing condition differences between particular areas of the field, recommended planting or harvesting dates, operational settings for farm equipment such as combines or tractors, estimates of future yields, and/or the like.

In some embodiments, plant insight logic included in compute device 104 may be configured to generate the plant insights. Plant insight logic may be implemented as software comprising one or more instructions to be executed by one or more processors included in compute device 104 (and/or a remotely located server/compute device if compute device 104 is resource constrained or plant insights are to be generated off-site). In alternative embodiments, plant insight logic (or a portion thereof) may be implemented as firmware or hardware such as, but not limited to, an application specific integrated circuit (ASIC), programmable array logic (PAL), field programmable gate array (FPGA), and the like included in the compute device 104 (and/or remotely located server/compute device).

In some embodiments, at block 214, a plant insight report that includes any of the plant insight data discussed above may also be generated and displayed/presented to the user 110. If the plant insights include time sensitive recommendations, for example, user 110 may take action while in the field.

The generated plant insights may be saved locally and/or remotely, at block 216. Such saved data may be associated with one or more of the raw data, processed raw data, ground truth labeled data, processed ground truth labeled data, particular plants, particular fields, particular geo-locations, and/or the like.

Figure 3:
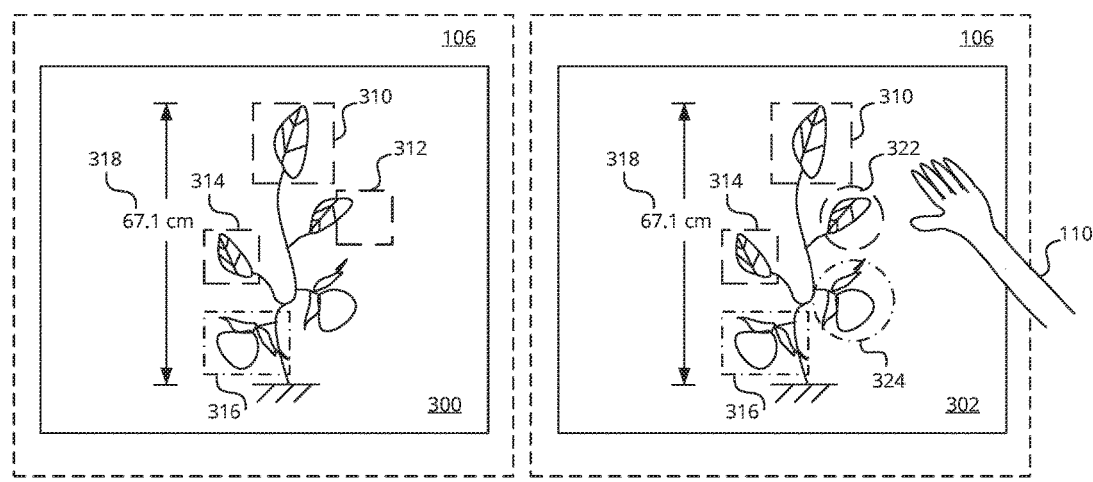
FIG. 3 depicts example images associated with acquisition of semi-autonomous ground truth labels for a plant, according to some embodiments.

In alternative embodiments, semi-autonomous ground truth labels may be generated comprising a combination of autonomously predicted ground truth labels and manually confirmed and/or supplemented ground truth labels. FIG. 3 depicts example images 300 and 302 associated with acquisition of semi-autonomous ground truth labels for the plant 114, according to some embodiments. Images 300 and 302 may be displayed on the user interface device 106.

In particular, image 300 may be initially displayed on the user interface device 106 after acquisition of raw data associated with plant 114. Labels 310, 312, 314, 316, 318 included in image 300 comprise autonomously predicted ground truth labels of phenotypic traits of the plant 114. Labels 310-318 associated with plant 114 may be generated by one or more computerized models developed to automatically identify or extract phenotypic traits by analyzing raw data associated with the plant 114. The computerized models may have been pre-trained or -configured by sets of raw data and associated ground truth labels of phenotypic traits (such as sets of manual ground truth labels generated in connection with FIG. 2). Details of the computerized models, techniques, algorithms, or the like will be further discussed in connection with FIGS. 4 and 5.

Labels 310, 312, and 314 predict ground truth labels of respective leaves of the plant 114, label 316 predicts a ground truth label of a fruit of the plant 114, and label 318 predicts a ground truth label of the height of the plant 114.

Upon viewing image 300, user 110 may confirm, check, augment, correct, supplement, and/or otherwise manually complete generation of high confidence or accurate ground truth labels for the plant 114. Image 302 depicts image 300 after inputs made by the user 110 on the user interface device 106. In image 302, new label 322 may comprise a modification of label 312 associated with a leaf of the plant 114 made by the user 110. Label 312 may have been modified because it only partially identifies the leaf; hence, the only a partial size, color, location, and/or other traits may have been detected for that leaf. New label 324 identifies one or more traits associated with a fruit that was not detected by the model (see absence of a label for the fruit in image 300). Thus, a complete set of ground truth labels for plant 114 may be generated, partly autonomous and partly manually generated.

Figure 4:
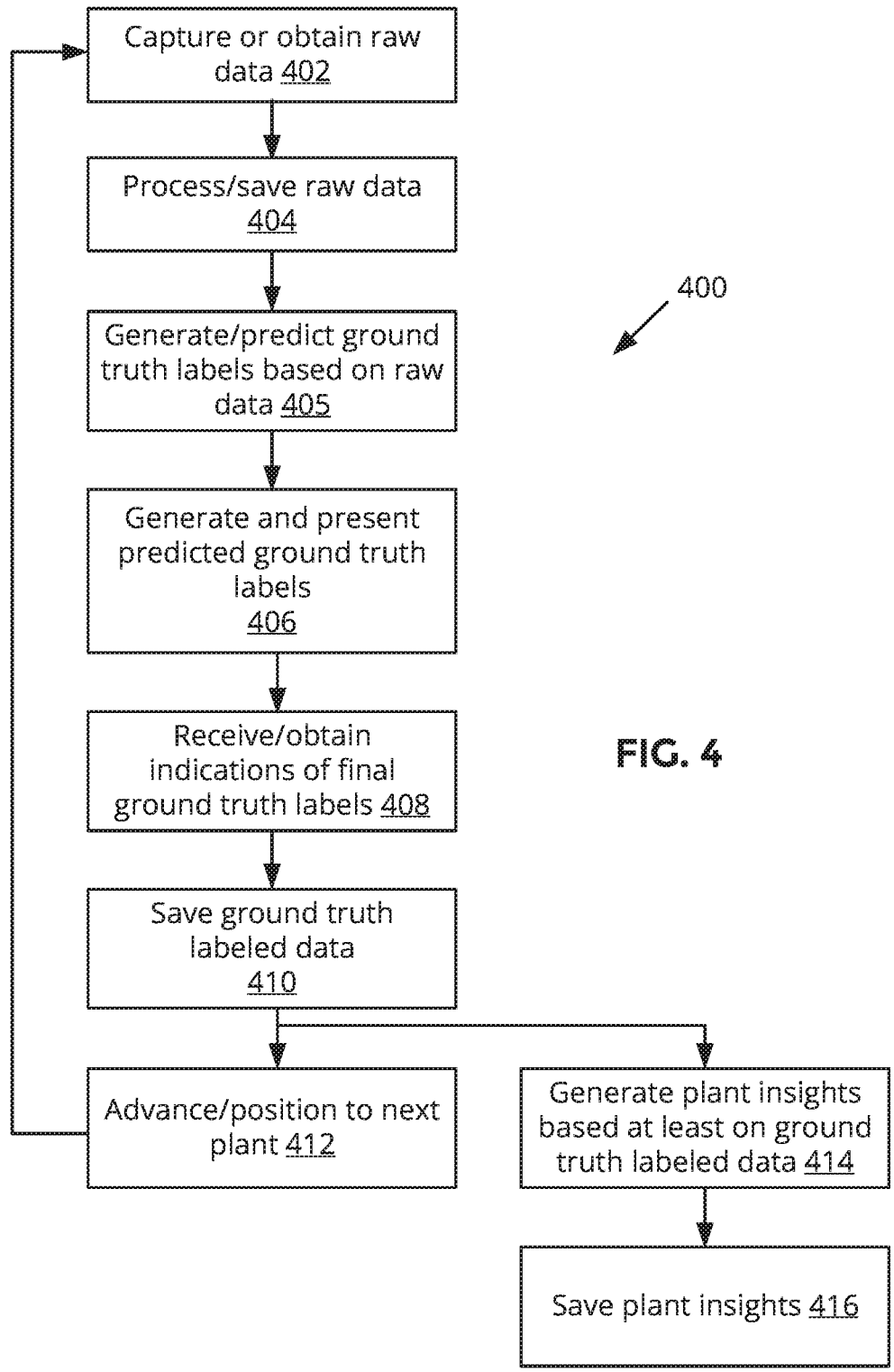
FIG. 4 depicts an example process for semi-autonomous generation of real time (or near real time) ground truth labels, according to some embodiments.

FIG. 4 depicts an example process 400 for semi-autonomous generation of real time (or near real time) ground truth labels, according to some embodiments. In some embodiments, blocks 402 and 404 may be similar to respective blocks 202 and 204 of FIG. 2.

With raw data associated with a particular plant (e.g., plant 114) acquired, processed (as needed), and saved, process 400 may proceed to block 405. At block 405, ground truth label prediction logic included in compute device 104 (and/or remote server/compute device) may be configured to autonomously extract or predict ground truth labels of phenotypic traits associated with the particular plant based on raw data in block 404.

Ground truth label prediction logic may comprise one or more computerized models that have been pre-trained or -configured with sets of raw data and associated ground truth labels of phenotypic traits that are of high confidence level or accuracy. Raw data associated with the plant of interest may comprise the inputs to the models, and in response, the models may analyze the raw data to extract, predict, identify, or determine phenotypic traits of the plant of interest. Models, techniques, algorithms, or the like that may be used or trained may include, but are not limited to, one or more of: optical flow techniques that may be used to determine the segments or parts of the plant present in the raw data; computer vision techniques; convolutional neural net or network (CNN) may be used to analyze image raw data; recurrent neural net or network (RNN) may be used to extract plant traits present in the raw data; machine learning dataflow libraries (e.g., TensorFlow which is available as an open-source software library for Machine Intelligence from TensorFlow Community) may be used to facilitate use of machine learning or deep learning models; machine learning models/systems; deep learning models/systems; and/or the like.

Ground truth label prediction logic may be configured to generate ground truth labels that may be similar to and/or more extensive than human generated ground truth labels. For example, if the raw data includes 3D point cloud plant data associated with the plant of interest, ground truth label prediction logic may be configured to automatically extract 3D architectural/structural traits of the plant of interest using the 3D point cloud plant data.

In some embodiments, ground truth label prediction logic may be implemented as software comprising one or more instructions to be executed by one or more processors included in compute device 104 (and/or remote server/ compute device). In alternative embodiments, ground truth label prediction logic (or a portion thereof) may be implemented as firmware or hardware such as, but not limited to, an application specific integrated circuit (ASIC), programmable array logic (PAL), field programmable gate array (FPGA), and the like included in the compute device 104 (and/or remotely located server/compute device).

Next, at block 406, compute device 104 may be configured to generate and present, on the user interface device 106, the predicted ground truth labels of block 405 in a format that may be accessible by the user 110. One or more images, graphs, textual or numerical data, data tables, and/or the like may be presented. For instance, the predicted ground truth labels may be visually displayed along with an image of the plant of interest, such as image 300. User interface device 106 may prompt user 110 to review the predicted ground truth labels and accept, supplement, and/or modify the predictions.

At block 408, user interface device 106 and compute device 104 may be configured to receive inputs from the user 110 associated with finalizing ground truth labels. As discussed above, user 110 may accept, confirm, modify, and/or otherwise provide an indication about one or more of the predicted ground truth labels, and the user 110 may also add new ground truth labels, such as shown in image 302. User 110 may provide his/her inputs from viewing the presentation of block 406 (e.g., image 300) and/or by performing direction observations or measurements of the actual plant (e.g., measuring or inspecting plant 114).

In some embodiments, blocks 405, 406, and 408 may be performed in a field environment, contemporaneous with or in real time (or near real time) to block 402. Blocks 402, 405, 406, and 408 may be performed during a single time within the field and without leaving the field and returning.

The combination of autonomously predicted ground truth labels supplemented with human input, referred to as semi-autonomous ground truth labels, may be saved, indexed, etc. by the compute device 104, at block 410. Process 400 may then proceed to block 412 to position the system 100 to the next plant and return to block 402 to capture raw data associated with the next plant. Plant insights may also be generated and saved, at respective blocks 414, 416, based on the saved ground truth labeled data of block 410. Blocks 410-416 may be similar to blocks 210-216 of FIG. 2 except the ground truth labeled data comprises the semi-autonomous ground truth labels finalized at block 408.

In other alternative embodiments, fully autonomous ground truth labels may be generated based on the raw data. In this case, system 100 may be configured to generate final ground truth labels based on raw data without human input. System 100 may also be configured to collect raw data, process the collected raw data in real time (or near real time), and extract/generate associated ground truth labels in real time (or near real time) without human input. For example, at least a portion of the system 100 may comprise an unmanned ground vehicle (UGV) or unmanned aerial vehicle (UAV). Although system 100 is depicted in FIG. 1 as a single mobile platform, system 100 may comprise two or more mobile platforms and one or more (or portions of) sensors 102, compute device 104, and user interface device 106 may be distributed between the two or more mobile platforms comprising the system 100. A first portion of system 100, for example, may comprise a ground platform and a second portion of system 100 may comprise an aerial platform.

Figure 5:
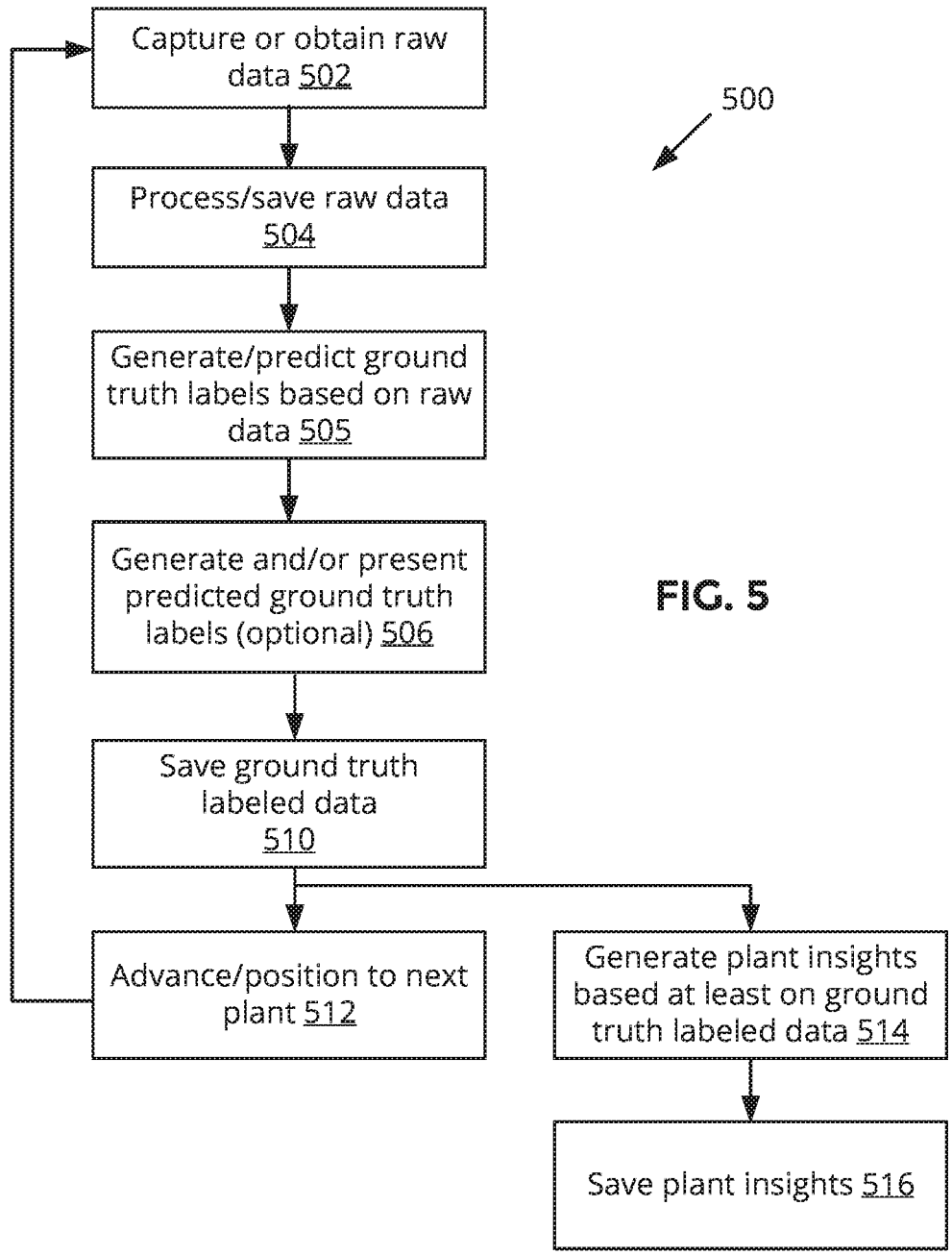
FIG. 5 depicts an example process for autonomous generation of real time (or near real time) ground truth labels, according to some embodiments.

FIG. 5 depicts an example process 500 for generation of autonomous ground truth labels of plant phenotypic traits for a plant of interest (e.g., plant 114), according to some embodiments. Raw data associated with the plant of interest may be acquired, processed (optional), and saved using system 100 at blocks 502 and 504. Blocks 502 and 504 may be similar to respective blocks 202 and 204.

Next, at block 505, ground truth label prediction logic included in compute device 104 (and/or remote server/compute device) may be configured to generate, predict, or extract ground truth labels of phenotypic traits associated with the plant of interest based on the raw data of block 504. Block 505 may be similar to block 405. The model configured to perform automatic plant trait extraction from the raw data may be the same or similar to the model used to obtain predicted ground truth labels in block 405. In some embodiments, the model of block 505 may comprise a more trained version of the model of block 405 such that the model of block 505 may predict ground truth labels that are of higher confidence or accuracy, types, and/or greater granularity than ground truth labels that may be predicted by the model of block 405. In some embodiments, process 400 (or a portion thereof) may be considered to be part of the training phase of the model used in block 505.

As discussed above, the model may be trained to extract or identify any of a variety of plant traits. As an example, if the raw data sensed in block 502 is associated with plants 118 and 120, one of the analyses that may be performed of the raw data may be to disambiguate or classify the plant structures/parts belonging to plant 118 from those belonging to plant 120. The base, branches, and/or stalks may be identified and tracing may be performed thereon to determine the extent of respective plants 118, 120.

Ground truth labels generated in block 505 may be generated in real time, near real time, or contemporaneous with acquisition of the raw data. Ground truth labels may be generated on-site while system 100 is in the crop field.

Next, at block 506, compute device 104 may be configured to generate and/or present the ground truth labels generated in block 505 along with possible associated information. For example, if the user 110 may be in the field along with system 100, real time (or near real time) use of the raw data may be demonstrated by displaying the ground truth labels along with an image of the plant of interest. Block 506 may be optional if there is no human operator in the field, for example.

Once the ground truth labels have been generated, since they comprise extracted phenotypic trait data at high confidence, such data and/or a version configured for presentation may be saved at block 510 without review, correction, or augmentation by the user 110. Then system 100 may be repositioned, at block 512, to capture raw data associated with the next plant, process 500 returning to block 502. Blocks 510 and 512 may be similar to respective blocks 210 and 212. In some embodiments, block 512 may occur simultaneous with any of blocks 504, 505, 506, or 510.

At block 514, plant insights may also be automatically generated based on the ground truth labels saved in block 510, and such plant insights may be saved at block 516. Blocks 514, 516 may be similar to respective blocks 214, 216. Ground truth labels generated in block 505 and referred to in connection with blocks 506-516 may also be referred to as autonomously extracted phenotypic traits based on the raw/sensor data associated with the plant of interest.

In this manner, a plurality of plant phenotypic traits associated with a plant or crop may be accurately determined in real time (or near real time) to acquisition of data sensed about the plant or crop. Varying degrees of autonomous generation of the plant phenotypic traits may be possible, depending on availability of an automatic analysis system, the accuracy or confidence level of the automatic analysis system, availability of knowledgeable human operators to manually acquire plant phenotypic traits, and/or the like. Plant insights based on the determined plant phenotypic traits may also be generated in real time (or near real time) to determination of the plant phenotypic traits. Diagnosing a plant disease (e.g., based on leaf color, size, shape, or other plant characteristic) and formulating a treatment plan or estimating when a fruit plant will be ready to for harvest (e.g., based on size, color, or shape of fruit growing on the plant) is an example of plant insights that may be provided.

Figure 6:
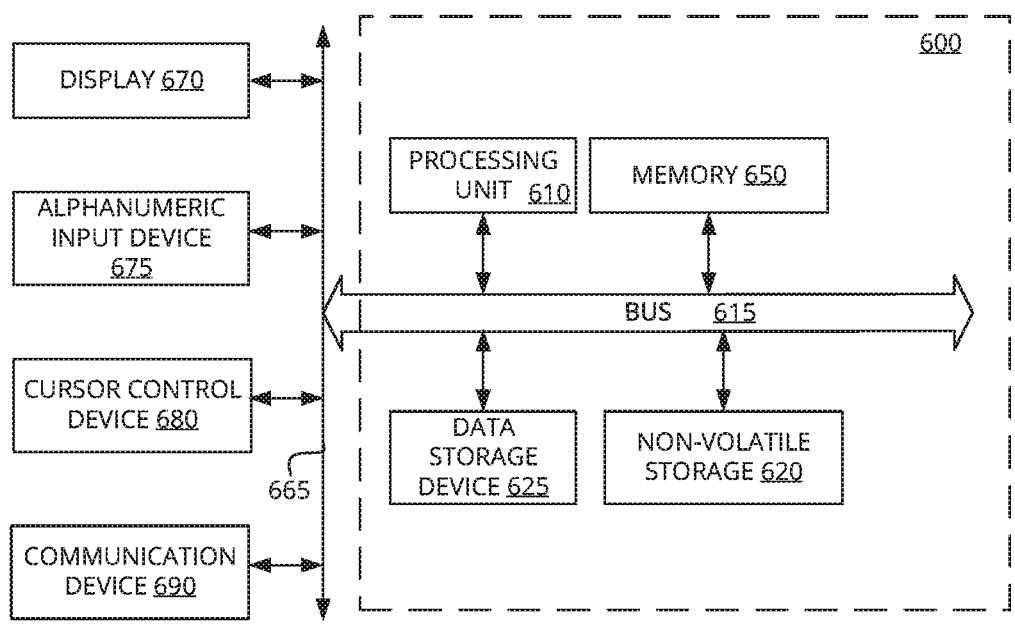
FIG. 6 depicts an example device that may be implemented in the system of FIG. 1 of the present disclosure, according to some embodiments.

FIG. 6 depicts an example device that may be implemented in the system 100 of the present disclosure, according to some embodiments. The device of FIG. 6 may comprise at least a portion of any of sensors 102, compute device 104, user interface device 106, remote servers, remote databases, and/or remote resources to the system 100. Platform 600 as illustrated includes bus or other internal communication means 615 for communicating information, and processor 610 coupled to bus 615 for processing information. The platform further comprises random access memory (RAM) or other volatile storage device 650 (alternatively referred to herein as main memory), coupled to bus 615 for storing information and instructions to be executed by processor 610. Main memory 650 also may be used for storing temporary variables or other intermediate information during execution of instructions by processor 610. Platform 600 also comprises read only memory (ROM) and/or static storage device 620 coupled to bus 615 for storing static information and instructions for processor 610, and data storage device 625 such as a magnetic disk, optical disk and its corresponding disk drive, or a portable storage device (e.g., a universal serial bus (USB) flash drive, a Secure Digital (SD) card). Data storage device 625 is coupled to bus 615 for storing information and instructions.

Platform 600 may further be coupled to display device 670, such as a cathode ray tube (CRT) or a liquid crystal display (LCD) coupled to bus 615 through bus 665 for displaying information to a computer user. In embodiments where platform 600 provides computing ability and connectivity to a created and installed display device, display device 670 may display the images overlaid with the crop fields/sub-fields information as described above. Alphanumeric input device 675, including alphanumeric and other keys, may also be coupled to bus 615 through bus 665 (e.g., via infrared (IR) or radio frequency (RF) signals) for communicating information and command selections to processor 610. An additional user input device is cursor control device 680, such as a mouse, a trackball, stylus, or cursor direction keys coupled to bus 615 through bus 665 for communicating direction information and command selections to processor 610, and for controlling cursor movement on display device 670. In embodiments utilizing a touch-screen interface, it is understood that display 670, input device 675, and cursor control device 680 may all be integrated into a touch-screen unit.

Another component, which may optionally be coupled to platform 600, is a communication device 690 for accessing other nodes of a distributed system via a network. Communication device 690 may include any of a number of commercially available networking peripheral devices such as those used for coupling to an Ethernet, token ring, Internet, or wide area network. Communication device 690 may further be a null-modem connection, or any other mechanism that provides connectivity between platform 600 and the outside world. Note that any or all of the components of this system illustrated in FIG. 6 and associated hardware may be used in various embodiments of the disclosure.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit (ASIC) or otherwise.

A tangible machine-readable storage medium includes any mechanism that provides (e.g., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A method comprising:
   acquiring sensor data associated with a plant growing in a field, wherein the sensor data is acquired from one or more of an optical sensor, an acoustic sensor, a chemical sensor, a geo-location sensor, an environmental sensor, and a weather sensor;
   analyzing the sensor data to extract, while in the field, one or more phenotypic traits associated with the plant from the sensor data;
   indexing, while in the field, the one or more phenotypic traits to one or both of an identifier of the plant or a virtual representation of a part of the plant;
   determining one or more plant insights based on the one or more phenotypic traits, wherein the one or more plant insights includes information about one or more of a health, a yield, a planting, a growth, a harvest, a management, a performance, and a state of the plant; and
   generating a plant insights report that includes one or more of the health, the yield, the planting, the growth, the harvest, the management, the performance, and the state of the plant;
   wherein analyzing the sensor data includes:
      predicting the one or more phenotypic traits based on the sensor data and a computerized model;
      displaying indications of the one or more phenotypic traits predicted; and obtaining a confirmation, modification, or addition indication from the user for at least one of the indications of the one or more phenotypic traits predicted based on direct observation of the plant in the field by the user; and wherein the one or more phenotypic traits extracted comprises the one or more phenotypic traits predicted as confirmed, modified or added in accordance with the obtained confirmation, modification, or addition indication.

2. The method of claim 1, wherein the computerized model includes a machine learning system, a deep learning system, an optical flow technique, a computer vision technique, a convolutional neural network (CNN), a recurrent neutral network (RNN), or a machine learning dataflow library, and wherein analyzing the sensor data comprises autonomously predicting the one or more phenotypic traits.

3. The method of claim 1, wherein determining the one or more plant insights comprising determining the one or more plant insights while in the field.

4. The method of claim 1, further comprising identifying, while in the field, one or more metadata associated with the plant or a condition of an environment proximate to the plant based on the sensor data.

5. The method of claim 4, wherein the condition of the environment proximate to the plant comprises soil properties, soil chemical composition, light, solar characteristics, temperature, or humidity, and wherein determining the one or more plant insights comprises determining the one or more plant insights based on the one or more phenotypic traits and the condition of the environment proximate to the plant.

6. The method of claim 1, wherein the one or more phenotypic traits comprises physical attributes of the plant, and wherein the plant comprises a crop plant, a fruit bearing plant, a vegetable bearing plant, or a seed bearing plant.

7. The method of claim 1, wherein acquiring the sensor data comprises acquiring the sensor data using a human-operated vehicle, an unmanned aerial vehicle (UAV), or an unmanned ground vehicle (UGV).

8. One or more computer-readable storage media comprising a plurality of instructions to cause an apparatus, in response to execution by one or more processors of the apparatus, to:

acquire sensor data associated with a plant growing in a field, wherein the sensor data is acquired from one or more of an optical sensor, an acoustic sensor, a chemical sensor, a geo-location sensor, an environmental sensor, and a weather sensor;

analyze the sensor data to extract, while in the field, one or more phenotypic traits associated with the plant from the sensor data;

index, while in the field, the one or more phenotypic traits to one or both of an identifier of the plant or a virtual representation of a part of the plant; and determine one or more plant insights based on the one or more phenotypic traits, wherein the one or more plant insights includes information about one or more of a health, a yield, a planting, a growth, a harvest, a management, a performance, and a state of the plant;

wherein analyzing the sensor data includes:
predicting the one or more phenotypic traits based on the sensor data and a computerized model;
displaying indications of the one or more phenotypic traits predicted; and
obtaining a confirmation, modification, or addition indication from the user for at least one of the indications of the one or more phenotypic traits predicted based on direct observation of the plant in the field by the user; and wherein the one or more phenotypic traits extracted comprises the one or more phenotypic traits predicted as confirmed, modified or added in accordance with the obtained confirmation, modification, or addition indication.

9. The computer-readable storage medium of claim 8, further comprising to cause the apparatus, in response to execution by the one or more processors of the apparatus, to generate a plant insights report that includes one or more of the health, the yield, the planting, the growth, the harvest, the management, the performance, and the state of the plant.

10. The computer-readable storage medium of claim 8, wherein the computerized model includes a machine learning system, a deep learning system, an optical flow technique, a computer vision technique, a convolutional neural network (CNN), a recurrent neutral network (RNN), or a machine learning dataflow library, and wherein analyzing the sensor data comprises autonomously predicting the one or more phenotypic traits.

11. The computer-readable storage medium of claim 8, further comprising to cause the apparatus, in response to execution by the one or more processors of the apparatus, to identify, while in the field, one or more metadata associated with the plant or a condition of an environment proximate to the plant based on the sensor data.

12. The computer-readable storage medium of claim 11, wherein the condition of the environment proximate to the plant comprises soil properties, soil chemical composition, light, solar characteristics, temperature, or humidity, and wherein determining the one or more plant insights comprises determining the one or more plant insights based on the one or more phenotypic traits and the condition of the environment proximate to the plant.

13. The computer-readable storage medium of claim 8, wherein the one or more phenotypic traits comprises physical attributes of the plant, and wherein the plant comprises a crop plant, a fruit bearing plant, a vegetable bearing plant, or a seed bearing plant.

14. The computer-readable storage medium of claim 8, wherein to acquire the sensor data comprises to acquire the sensor data using a human-operated vehicle, an unmanned aerial vehicle (UAV), or an unmanned ground vehicle (UGV).

* * * * *